United States Patent
Kaye et al.

(10) Patent No.: US 6,437,211 B2
(45) Date of Patent: *Aug. 20, 2002

(54) METHODS FOR TREATMENT AND DISPOSAL OF REGULATED MEDICAL WASTE

(75) Inventors: Gordon I. Kaye, Troy; Peter B. Weber, Delmar, both of NY (US)

(73) Assignee: Waste Reduction by Waste Reduction, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/882,806

(22) Filed: Jun. 14, 2001

Related U.S. Application Data

(63) Continuation-in-part of application No. 09/171,447, filed as application No. PCT/US97/06616 on Apr. 21, 1997.
(60) Provisional application No. 60/036,665, filed on Apr. 22, 1996.

(51) Int. Cl.$^7$ ............................... A61L 2/18; A62D 3/00
(52) U.S. Cl. .......................... 588/205; 422/28; 422/32; 210/751; 210/764
(58) Field of Search ................................. 588/205, 258, 588/901; 422/28, 32, 33, 36; 241/606; 554/8, 12; 210/749, 751, 764, 766

(56) References Cited

U.S. PATENT DOCUMENTS

| 5,332,532 A | 7/1994 | Kaye et al. .................... 588/16 |
| 5,384,092 A | 1/1995 | Sawhill et al. ................. 422/32 |
| 5,387,350 A | 2/1995 | Mason ........................ 210/754 |
| 5,422,074 A | 6/1995 | Schmidt ....................... 422/28 |

FOREIGN PATENT DOCUMENTS

| AT | 8202169 | 7/1983 |
| EP | 13659 | 7/1980 |

*Primary Examiner*—Steven P. Griffin
*Assistant Examiner*—Eileen E. Nave
(74) *Attorney, Agent, or Firm*—Heslin Rothenberg Farley & Mesiti P.C.; Martha L. Boden, Esq.

(57) ABSTRACT

A method for safely treating and disposing of infectious biomedical waste and other hazardous materials is disclosed. The method involves alkaline hydrolysis of infectious agents contained in regulated medical waste or hazardous waste solutions. The infectious waste is immersed into a highly basic solvent (>130° C.,>2.79 atm) until the hydrolyzable matter is fully digested, thereby forming a sterile solution and sterile solid waste. The sterile solution and solid waste may then be disposed of through standard means, such as in a sanitary sewage system or local landfill facility. The method also provides for the treatment of lipid soluble hazardous material contained in the regulated medical waste.

22 Claims, 4 Drawing Sheets

METHODS FOR TREATMENT AND DISPOSAL OF REGULATED MEDICAL WASTE

CROSS-REFERENCE TO RELATED APPLICATION

The present application is a continuation in part application of earlier copending U.S. patent application Ser. No. 09/171,447, filed Oct. 20, 1998, which is a 371 of PCT/US97/06616, filed Apr. 21, 1997, and claims benefit of U.S. Provisional Application 60/036,665, filed Apr. 22, 1996.

TECHNICAL FIELD

The present invention relates to the field of waste disposal. More particularly, the invention relates to methods for safely treating and disposing of infectious biomedical waste and other hazardous materials.

BACKGROUND OF THE INVENTION

Today hospitals and other health-care organizations produce considerable amounts of infectious waste. This type of waste includes surgical gowns, surgical gloves, needles, instruments, glass, culture dishes, and other disposable matter exposed to blood and other body fluids of patients. Such waste is classified as "regulated medical waste" under federal regulations, disposal of which must comply with strict governmental regulations. As used herein, the term "regulated medical waste" refers to infectious waste, to waste containing infectious agents, as defined below, and to any waste that poses a threat of transmission of infection to humans or animals, i.e. potentially containing infectious agents capable of causing infection in humans or animals. Such regulated medical waste may include, but is not limited to, tissue, cloth, plastic, paper, animal carcasses, bedding and other matter potentially containing infectious agents.

Recently, Health-care organizations as well as Regulatory Agencies have been concerned with the adequacy of existing cleaning and disposal methods. It has been discovered that some potentially harmful cells, such as prokaryotes, or harmful proteins may survive standard autoclaving procedures. Thus, more effective sterilization techniques have been sought for treating solid infectious biomedical waste, i.e., regulated medical waste.

In addition, universities and other research facilities likewise produce a significant level of such waste. In conducting experiments in cell lines, tissues or upon animals, it is common to introduce dyes, toxic chemicals or infectious agents into the test subject. After completion of the test and analysis, due to the introduction of infectious agents or hazardous materials, the remaining tissue or animal carcass falls under the classification of regulated medical waste. In addition, animal waste, animal bedding, handling materials and other matter exposed to animal body fluids or excretions may also need to be treated as infectious or hazardous waste, thus requiring disposal in accordance with applicable governmental regulations.

In addition, it is common for health care organizations today to clean materials, instruments or surface areas exposed to infectious agents, including zoonotic agents, with disinfectants such as formaldehyde or glutaraldehyde. Spent cleaning solution is considered hazardous liquid waste and must be disposed of in compliance with government regulations. The cost of disposing of such waste, on an institutional basis, can be quite costly. In addition, formaldehyde, glutaraldehyde, phenols and like materials are commonly used for embalming tissues and in fixation of infectious biological materials. Thus, these tissues and the fixative agents must likewise be disposed of in compliance with government regulations.

Currently, the two methods commonly used in disposing of hazardous waste and regulated medical waste are incineration and burial. Presently Federal law imposes strict regulations for incineration of hazardous waste and infectious biomedical waste. However, incineration may be further limited by state and local agencies. For example, incineration of regulated medical waste or other hazardous waste is not available at all in some jurisdictions such as the major metropolitan areas of New York City, San Francisco and Chicago. Furthermore, the general process of incineration itself, even when no hazardous materials or regulated medical wastes are involved, is subject to additional regulations, such as those requiring a direct license from a state or local environmental agency. Additionally, future increases in the requirements for incinerator designs and function under clean air regulations put in doubt the continued availability of incineration as a method of disposing such wastes.

Presently, the only real alternative to incineration is autoclaving the solid waste and then burying the waste material in a licensed waste disposal facility. Currently there are a limited number of such sites in the United States. It is extremely costly to dispose of infectious medical waste by this method. Further, one will appreciate that the cost is exceedingly high for waste that comprises matter which, but for the potential infectious agents, could be disposed of using less costly local disposal facilities. Due to the extremely high cost associated with land burial and the limitations on access to licensed land burial sites, the feasibility of land burial as a method of disposing of such waste remains an ever growing concern for research and health-care facilities.

The known methods of disposing of regulated medical wastes generated by many universities, health-care and research facilities faces an uncertain future under the ever narrowing scope of environmental laws. Furthermore each is extremely costly, putting an unneeded drain on the already strained resources of universities, health-care organizations and research facilities. Thus, a need exists for methods for disposing of infectious bio-medical wastes and other hazardous materials which is safe, environmentally friendly and less expensive than existing disposal means.

SUMMARY OF INVENTION

The aforsaid needs are satisfied and the limitations of the prior art overcome, in accordance with the principles of the present invention, by providing a method for producing safely disposable compositions from regulated medical waste. This method for treating regulated medical waste comprises the steps of providing a highly basic solvent, immersing the regulated medical waste within the highly basic solvent, and heating. The regulated medical waste contains infectious agents, which comprise hydrolyzable material (i.e. biological tissues, cells, or cell components containing proteins or lipids capable of undergoing hydrolysis or saponification in the highly basic solvent). Furthermore, the infectious agents are capable of causing infection in humans or animals and are selected from the group consisting of bacteria, organisms, and proteinaceous material.

To assure degradation of all infectious wastes, including prokaryotes, the heating step comprises heating the highly basic solvent and immersed regulated medical waste to a temperature greater than 130° C. and under an absolute pressure greater than 2.79 atmospheres (gauge pressure >1.79 atm) and for a time sufficient to digest the hydrolyzable material. A sterile solution comprising non-toxic biodegradable materials and containing sterile solid waste free of infectious agents is produced. Degradation of the regulated medical waste preferably involves treating the waste at a temperature around 135° C. and under an absolute pressure about 3.1 atmospheres (gauge pressure about 2.1 atm), and more preferably, around 150° C. to 155° C. and about 5 atmospheres (gauge pressure about 4 atmospheres). At a temperature around 180° C., the corresponding pressure will be about 10 atmospheres (gauge pressure about 9 atm). Generally, it is preferable not to exceed temperatures of about 180° C. Unless indicated otherwise, pressures herein are absolute in atmospheric units, and the corrresponding gauge pressure reading may be calculated by subtracting 1 atmosphere from the absolute pressure.

The tissue or other matter potentially containing the infectious medical waste is allowed to remain within the highly basic solvent until the hydrolyzable matter is fully digested, thereby forming a sterile solution and sterile solid waste. The aqueous solution and any solid waste may then be disposed of through standard means, such as a sanitary sewage system and local landfill facilities. However, it will be appreciated that the amount of solid waste to be disposed of is substantially reduced by the present invention.

In another aspect, hazardous materials may be removed from the digest and separately disposed of in an appropriate manner, such as in a landfill designated for such hazardous wastes or in a specially licensed high temperature furnace. Paraffin or wax may be added to the regulated medical waste prior to or after digestion. Upon heating of the materials, the paraffin or wax melts and becomes distributed throughout the aqueous solution. After the waste has been fully digested and the aqueous solution is allowed to cool, the lipid-like materials separate out from and float to the surface of the aqueous phase where they resolidify upon cooling to room temperature. Lipid soluble waste materials may then be removed from the aqueous phase upon separation of the lipid phase because they have become incorporated within the lipid phase. Thus, removing the lipid phase from the solution effectively also removes lipid soluble hazardous materials not degraded or otherwise consumed in the alkaline treatment.

Accordingly, it is a principle object of this invention to provide a method for safely disposing of tissue and other matter containing infectious biological waste (i.e., regulated medical waste) and/or other hazardous materials. One advantage of this invention is that it allows for safe disposal of the regulated medical waste at significantly less expense to the research or health-care facility without harming or increasing the risk of harm to the environment. An additional advantage of this invention is that the method may be utilized without geographic limitations, satisfying existing governmental regulations at the federal, state and local level. Another advantage of this invention is that it preserves the ever shrinking area available in the land burial sites.

DETAILED DESCRIPTION OF THE INVENTION

Figure 1:
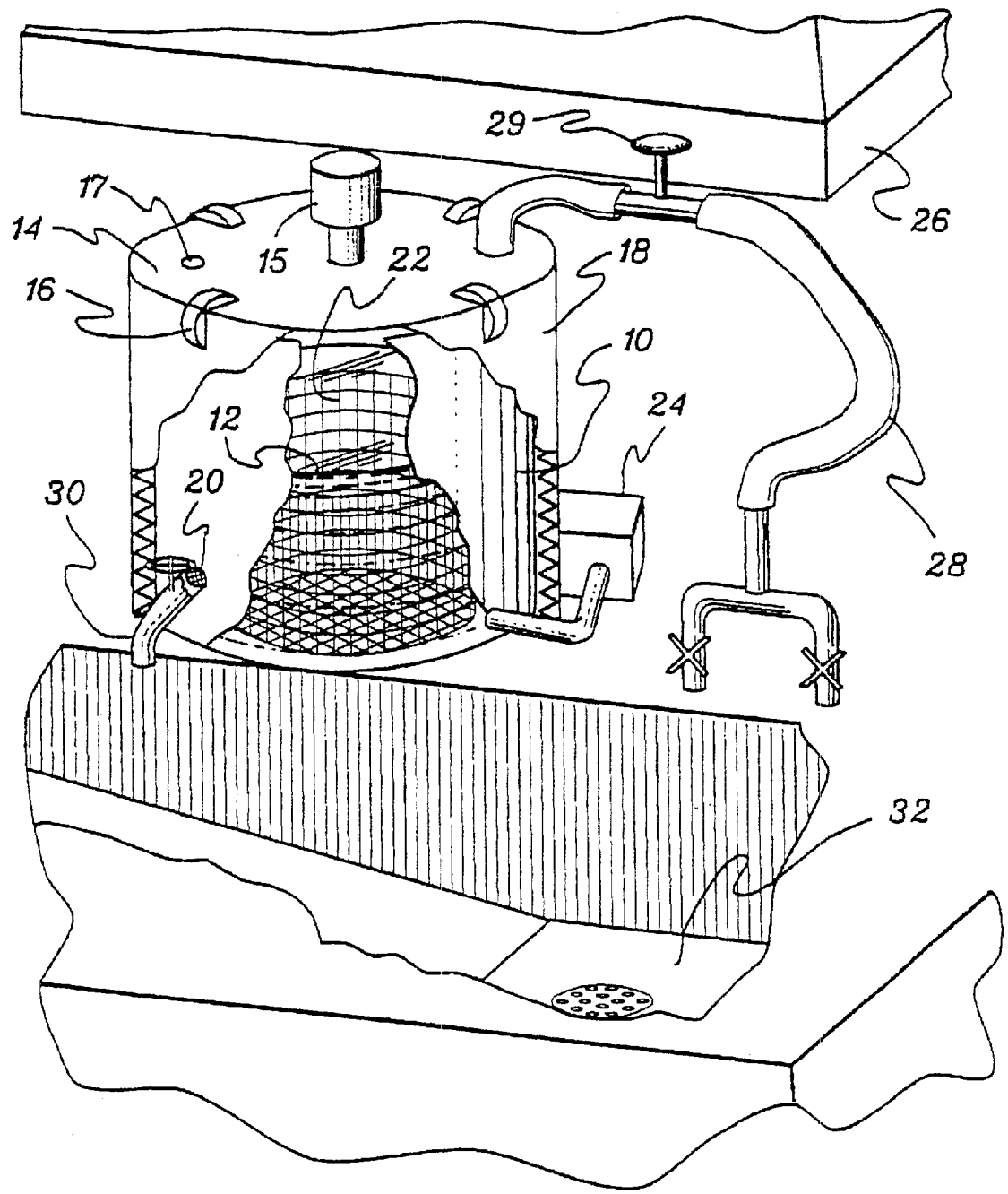
FIG. 1 shows a partial cut-away elevated view of an apparatus for practicing the present invention.

This invention involves a method for safely treating and disposing of matter containing infectious medical waste (i.e., regulated medical waste) and/or hazardous waste materials and is designed and intended to comply with all federal, state and local laws or regulations applicable to disposal of such wastes. In general, as is commonly known to those of skill in the art regarding various types of waste disposal, and as used herein, regulated medical waste does not contain radioactive material, and radioactive material does not contain regulated medical waste or infectious agents. In fact, as is commonly known, low level radioactive biological waste and infectious waste are two very different and completely separate waste streams regulated by different laws and regulations, as well as by different agencies. Processes intended for the treatment and disposal of one of these waste streams would not be expected to be applicable to the other.

With this in mind, in one aspect the method comprises the steps of immersing regulated medical waste, as defined above, within a highly basic solvent. The highly basic solvent is heated to a temperature greater than 130° C. under an absolute pressure greater than 2.79 atmospheres, preferably at a temperature around 135° C. and a pressure of about 3.1 atmospheres, but more preferably, at a temperature ranging from about 150° C. to about 155° C. and under an absolute pressure of about 5 atmospheres. Also, it is preferable to limit the temperature of the solvent to about 180° C., which corresponds to an absolute pressure of about 10 atmospheres. Furthermore, the reaction should be conducted in a sealed vessel, as described below, to reach the desired pressure. The pH of the highly basic solvent is preferably at least 12 and may vary up to 14. The aforementioned reaction conditions assure the complete degradation of all infectious wastes, including prokaryotes.

The tissue or other matter containing regulated medical waste, and optionally, hazardous waste material, as described below, is allowed to remain within the highly basic solvent until fully digested, thereby forming a sterile partially neutralized aqueous solution and sterile solid waste free of infectious agents, such as zoonotic agents or other hazardous materials. As used herein, "infectious agents" refers to bacteria or organisms or proteinaceous material capable of causing infection in humans or animals including, but not limited to, zoonotic agents and prokaryotes. "Sterile" and "sterilized" mean being free of infectious agents.

When the researcher is ready to dispose of the regulated medical waste, the waste is completely immersed in a highly basic solvent. Preferably, this solvent should have a pH of 12 to 14, and it may be comprised of a mixture of water and an alkali metal hydroxide, alkaline-earth metal hydroxide, or alkaline-earth metal oxide, such as calcium oxide. An aqueous solution of NaOH and/or KOH is preferred. An example of such a suitable highly basic solvent may consist of a 0.1 molar to 2.5 molar solution of NaOH in water, or approximately 0.4%–10% sodium hydroxide (by weight) in water. It has been discovered that gelation of the digest upon flushing with cold water may be avoided by using a highly basic solvent of 1.5 M NaOH or 1.0 molar KOH, or more. Calcium oxide is typically used at a pH of 12 in cases where there is no fat, for example, when the waste is meat, bone meal, blood, etc.

The waste should be immersed in enough highly basic solvent such that all biological tissues, cells, and cell components are completely digested; namely, hydrolyzing tissue proteins by breaking many of the peptide bonds and saponifying cell and tissue lipids. The terms "digested", "degraded", "neutralized", "treated" and forms thereof are interchangeable, as used herein. Also, as used herein, "hydrolyzable material" refers to biological tissues, cells or cell components that contain proteins or lipids capable of undergoing hydrolysis or saponification in the highly basic solvent. To ensure complete digestion of the hydrolyzable material, excess base is preferably used. One ratio assuring excess base to carry out the digestion of the waste to completion is a 1:10 ratio of sodium hydroxide to wet tissue weight. A further expression of this ratio is 40 kilograms NaOH in 500 liters $H_2O$ added to 500 kilograms tissue by weight. These ratios are given only as instruction as how to conduct the method stated herein and not to limit the nature of the invention; one using the method described herein may find ratios more economical and exact as the invention is practiced. It will be appreciated that lower ratios of alkali to waste may be used as the degree of non-organic matter, such as glass and plastic, increases.

If the reaction between the regulated medical waste and highly basic solvent were allowed to proceed at its natural rate, it may take an impractical amount of time. Conducting the reaction in a sealed vessel under increased pressure and temperature reduces the reaction time needed to completely digest the tissue, cells and cell components. Pressures greater than 2.79 atmospheres (and temperatures greater than 130° C.) are used in this regard, with pressures preferably up to about ten atmospheres (temperatures up to about 180° C.). Furthermore, detergents at a concentration of up to 1% by weight, examples being sodium lauryl sulfate or deoxycholate, may be added to the highly basic solvent. It should also be noted that, if no lipid soluble hazardous wastes are to be recovered, the addition of detergents also has the advantage of dispersing non-saponifiable lipids, and aiding in the sterilization of biological materials.

In addition, shredding the solid waste prior to immersion within the highly basic solvent reduces the reaction time by making more surface area accessible to the highly basic solvent. Still another method capable of reducing the reaction time is provided by supplying an excess of fresh highly basic solvent continuously onto the surface of the solid waste. This may be accomplished by agitating, circulating or stirring the solvent.

The reaction rate will ultimately depend on specific variables such as: the temperature of the solvent, pressure in the reaction vessels, nature of the waste and ratio of hydrolyzable material to the volume of the highly basic solvent. As the reaction rate will vary, the time that the waste must remain immersed in the highly basic solvent will also vary. However, regardless of the reaction rate, the waste should remain immersed within the highly basic solvent until the hydrolyzable matter is fully digested. Leaving the waste within the heated highly basic solution until complete digestion is achieved assures production of a sterile solution. Using excess base at a temperature greater than 130° C. and an absolute pressure greater than 2.79 atm, digestion will, in almost all instances, be complete after 8–9 hours. More preferably, however, the temperature should range from about 135° C. to 180° C. At a temperature ranging from about 150° C. to about 155° C. and at a pressure of about 5 atmospheres (65 psig), digestion may be complete in as little as 3 hours.

Once the animal tissue has been completely digested, neutralized, and treated, two types of solid debris often remain. As used herein, the term "sterile solid waste" includes the following two types of solid debris. The first type of debris consists of metal, rubber or plastic, such as surgical clips, sutures, glass, and other pieces of plastic or paper. Solid items such as these do not incorporate infectious medical waste and are completely sterilized after treatment. Thus, the treated solids may safely be disposed as ordinary sterile solid waste after being isolated from the solution and washed. The second type of solid debris remaining undissolved includes inorganic portions of the animal's skeletal structure. After treatment, all organic components of the skeletal structure are digested, leaving sterile calcium phosphate. The skeletal remains, when removed from the highly basic solvent and washed, are extremely friable and may be easily crushed. In fact, the skeletal remains are so friable that they may be crushed to form a disposable powder by such relatively simple means as manual application of pressure.

After the waste has been fully digested within the highly basic solvent and the solid debris removed, the remaining "sterile solution" will comprise a sterile mixture of alkali metal salts (or alkaline-earth metal salts) of amino acids, sugar acids, nucleotides, small peptides, fatty acids from lipids, phosphates from lipids and nucleic acid breakdown, soluble calcium salts, pigments, sugars, sugar alcohols, hydrocarbons and inorganic acids derived from the electrolytes normally found within tissue fluids. However, due to the heated alkaline treatment, infectious agents, including zoonotic agents and prokaryotes, are broken down into low molecular weight residues. Thus, it is entirely safe to dispose of the treated solution and solids using disposal means such as septic tanks, sewage systems, local landfills and other disposal means appropriate for the disposal of these simple non-hazardous materials.

Because the sterile solution at the end of the reaction process contains only non-toxic biodegradable materials, dilution of the solution may not be required for disposal. However, reducing the alkalinity the solution may be accomplished by diluting the solution, such as by adding excess water to the reaction vessel before it is discharged or as it is being discharged. With the majority of applications the resulting solution is well within the level of alkalinity that is safely disposable as sanitary sewage. Dilution may also be accomplished by one skilled in the art by calculation of the dilution of the specific unit of waste volume by the entire waste volume of the institution or manufacturing plant.

As indicated above, it is common to clean instruments and surface areas exposed to infectious agents with formaldehyde, glutaraldehyde and like agents. In addition, formaldehyde, glutaraldehyde, phenols and like materials are commonly used as fixating agents for biological tissues. Spent cleaning solution and fixatives are considered hazardous waste materials which must be disposed of in accord with applicable governmental regulations. As used herein, the term "hazardous waste solution" refers to spent cleaning solution or fixative and comprises infectious agents (containing hydrolyzable material) in solution with a material selected from the group consisting of formaldehyde, glutaraldehyde, phenols, mixtures of formaldehyde and glutaraldehyde, mixtures of formaldehyde and phenols, and mixtures of glutaraldehyde and phenols.

It has been discovered that spent cleaning solutions of formaldehyde, glutaraldehyde, phenols, and various combinations thereof, may be safely disposed of together with the digestion of regulated medical wastes (i.e., containing infectious agents). For example, up to 30 gallons of formaldehyde or glutaraldehyde, typically a 2–4% solution by weight, may be degraded in conjunction with 250 lbs. of tissue. Hazardous materials containing, for example, formaldehyde, glutaraldehyde, phenols, or mixtures thereof, and similar materials react in the above alkaline treatment to form harmless non-toxic materials. For example, when formaldehyde and phenol are in solution under the alkaline conditions a harmless inert plastic like material is formed. Also, the aldehydes by themselves react irreversibly with the tissue amino groups to form harmless products. Thus, the term "sterile solid waste" also includes the aforementioned plastic like material and harmless products.

However, not all hazardous materials will break down into inert by-products under the temperature and conditions described above. Thus, when the regulated medical waste material incorporates hazardous materials capable of withstanding the above conditions, additional steps must be undertaken to ensure degradation or extraction of the hazardous materials within the resulting solution. Lipid soluble hazardous materials, such as halogenated aliphatic and aromatic hydrocarbons, PCBs, chlorinated insecticides, many dyes and materials of like solubility may be extracted from the aqueous digest based on their solubility in lipids. Paraffin or wax, preferably in solid form, may be added to the waste material to be digested. Upon heating, the added materials melt and, with the aid of the soaps formed during alkaline saponification of fatty tissue, the materials become finely dispersed throughout the digest. After digestion is completed, the mixture is allowed to cool to room temperature (about 20° C. to about 25° C.), preferably without stirring. The lipid phase separates from the aqueous phase upon cooling and due to the solubility characteristics of the hazardous material, the lipid phase incorporates the lipid-soluble hazardous waste. The solid lipid phase floating on the top of the aqueous phase may then be easily removed from the digest, such as by straining. Thus, this method avoids the difficult and costly procedures associated with most liquid-liquid extractions. The resolidified solid lipid material, such as a paraffin cake, may then be disposed of accordingly. For example, where the solid lipid contains toxic or highly regulated materials, such as PCBs, the solid lipid extract may be disposed in the appropriate hazardous waste facility. This extraction process may be repeated, if necessary, for lipid-soluble compounds with partial solubility in the aqueous phase to allow for quantitative extraction of such compounds.

In this regard it is important to note that the volume of the hazardous material, and hence the cost in properly disposing of the same, has been considerably reduced since the large constituent of harmless biodegradable organic mater, such as peptides, sugars and amino acids have been separated from the toxic substance. Suitable paraffins and waxes include, but are not limited to ordinary household paraffins, carnauba wax, bees wax, mixtures of alkanes, and mixtures of hydrocarbons, long chain fatty acids, esters and alcohols that are solids at room temperature. In the event the hazardous material is insoluble in lipids, other known liquid-liquid extraction methods may be employed, the specific application of which will vary with regard to the particular hazardous material.

Disposal of the regulated medical waste should be prompt because the organic material begins to decompose immediately under room temperatures. Thus, the regulated waste must be dealt with soon after it is produced in order to avoid the creation of noxious odors and other health hazards. However, freezing of the regulated medical waste effectively prevents decomposition and the creation of noxious odors and health hazards. Thus, when it is not economical or practically feasible to dispose of the waste on a daily basis, the regulated medical waste may be frozen and stored in that condition until an appropriate time or amount of waste for disposal is acquired. Temporary storage of the waste by freezing may be accomplished by any refrigeration means capable of maintaining a temperature of 0 Celsius or below and capable of storing the amount of waste desired.

An apparatus for producing a safely disposable solution from regulated medical waste can be seen in reference to FIGS. 1–5, such an apparatus comprises the following elements: a sealable tank 10 with a highly basic solvent 12 therein, a permeable container 22 for storing regulated medical waste, a water supply means 28, a filtering means 20, a pressurizing and venting means 15 and a disposal means 32.

A preferred apparatus comprises a singular tank or vessel capable of containing a solution. The tank must be made of a material that is capable of withstanding the pH levels, temperatures and pressures utilized in this process, an example being stainless steel.

The reaction between the highly basic solvent 12 and the regulated medical waste, such as the tissue, cloth, paper or other matter, takes place within a tank 10. However, it is preferable for the reaction to occur within a closed reaction vessel in order to prevent $CO_2$ from the atmosphere from entering the reaction path. Thus, the tank 10 preferably has a sealing means 14 capable of withstanding the chemicals, temperatures and pressures utilized in this process, an example being stainless steel. Because absolute pressures greater than 2.79 atmospheres are utilized, the sealing means 14 must be pressure and air tight. This may be accomplished through the use of an alkali resistant gasket and a cover sealed to the tank with clamps 16. A pressurizing means 15 may be fitted to sealed tank 10 in order to increase the pressure therein. Furthermore, in an alternative embodiment the sealing means 14 may also contain a pressure gauge to monitor the reaction vessel, adjustable safety valves, and a sampling port 17 for measurement of the pH of the reaction mixture.

As discussed above, the process requires that the highly basic solution 12 be heated in order to assure degradation of all infectious agents and proper sterilization of the solid matter. Therefore, a heating means 18 is necessary to heat the highly basic solvent 12. Any heating means 18 commonly known and used today for heating solutions could be utilized in this process. One example of such a heating means 18 is a stainless steel heating jacket, in which heated water or steam circulates between the walls of a double walled tank, thereby heating the solution within the tank. Alternatively, the tank 10 may be fitted with an electric heating mantle, placed upon a hot pad, or fitted with an internal heating coil.

As discussed above, after the hydrolyzable waste has been fully digested, there often remains undigested solid debris, i.e. skeletal remains, glass or plastic. Thus, the preferred embodiment contains a filtering means 20, as shown in FIG. 1., for removing the solid debris before or during disposal of the sterile solution. An example of a suitable filter would be a 40 mesh/25.4 mm stainless steel screen. The filtering means 20 may be placed in combination with the removal means 30 such that the sterile solution is filtered as it is removed from the tank 10.

Figure 2:
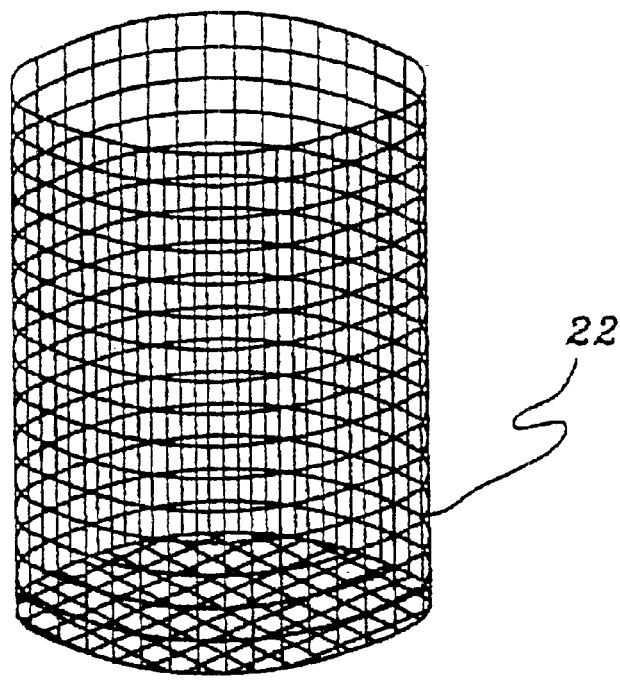
FIG. 2 shows a view of a screen mesh permeable container.
Figure 3:
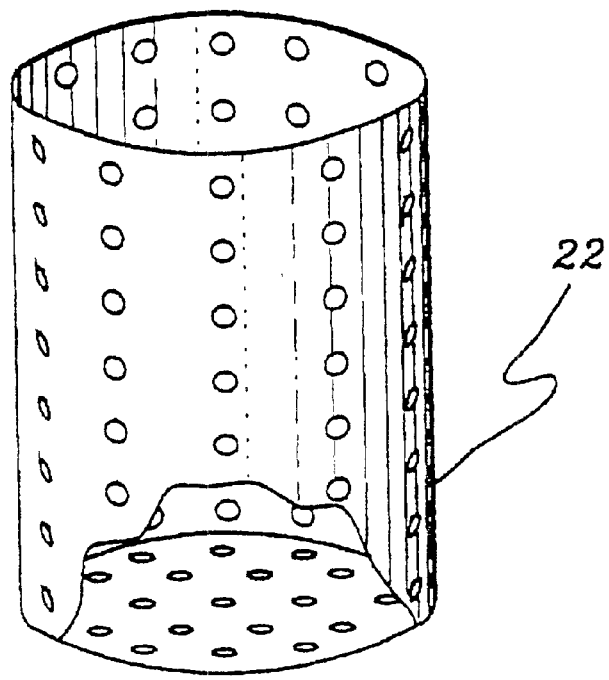
FIG. 3 shows an elevated view of a solid permeable container.
Figure 4:
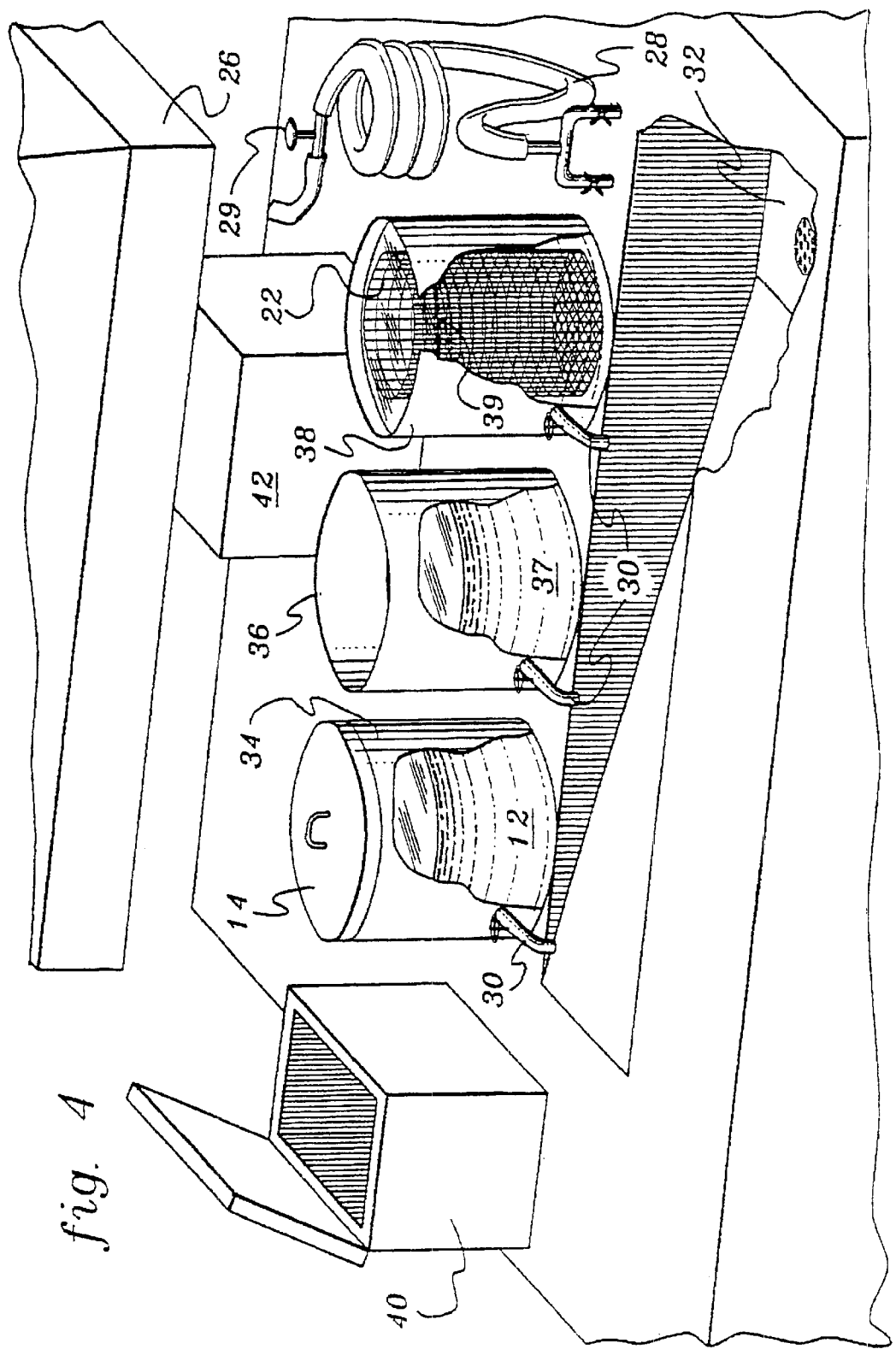
FIG. 4 shows a partial cut-away elevated view of an apparatus for practicing the present invention utilizing a plurality of tanks.

The apparatus may also have a permeable container 22 capable of holding the waste. The permeable container 22 may be utilized to immerse the waste within the highly basic solvent 12. This container may also act as the filtering means and/or a means for removing the solid sterile undigested debris. When the hydrolyzable matter is fully digested, the permeable container 22 may be removed, thereby removing the undigested solid debris remaining within the permeable container 22. The container should be made of a material capable of withstanding the pH levels, chemicals and temperatures involved in this process. In addition, the container should be permeable to liquids, small peptides and amino acids. An example of such a container can be seen in reference to FIG. 2 and FIG. 3. A container having 3.2 to 6.4 mm stainless steel screen mesh basket may suffice in practicing the method disclosed herein, such as can be seen in FIG. 2. When a large amount of waste is to be moved or held, the screen mesh basket should be reinforced with stainless steel bands. Alternatively, as seen in FIG. 3, the container may comprise of a solid stainless steel container with 3.2 or 6.4 mm holes drilled therein. These baskets may be shaped and sized to be removably fitted within of the above mentioned tank 10, with sufficient clearance to allow liquid to circulate over all surfaces of its contents. It is also possible that these containers could be sized such that they fit within the refrigeration means 40, as shown in FIG. 4, thereby reducing the work and components necessary to complete this process.

Because the natural reaction time is very slow, the preferred invention may also contain an agitating means 24 to help speed up the reaction rate by keeping the solvent or the substrate in motion while the reaction is taking place. A means for agitating or simply moving the solid undigested waste within the highly basic solvent 12 may accomplish its task by simply moving the permeable container 22 holding the animal remains. In addition, it is also possible to accomplish the same result by circulating the highly basic solvent 12. This may be accomplished by a wide variety of means well known in the art today, examples being mechanical stirrers or pumping means. However, any pump connected to the tank 10 via piping and valves must be capable of withstanding the temperatures, chemicals and pressure involved.

An exhaustion or ventilation means 26 such as a ventilated hood may be placed over the tank 10 and be positively ventilated in order to remove any excess carbon dioxide or noxious fumes produced by performing the method disclosed herein.

Depending on the size of the tanks 10 and the amount of hydrolyzable waste being digested, it may be possible to dilute the resulting sterile solution, directly within the tank 10 before draining said tank 10. However, not all tanks will be large enough to dilute the mixture created by the reaction. In such a case, dilution may occur simultaneously with draining of the tank 10. In either case, it is necessary to have a water supply means 28, preferably with a stop valve 29. The appropriate amount of water may be added as the solution drains or is pumped from the tank 10. This may be accomplished with any means for adding water, examples being any faucet, hose or lead connected to a water supply capable of delivering the rates necessary.

Finally, an apparatus for practicing the present invention may contain a means for emptying the contents 30 of the tank 10. One may simply use a drainage port and let gravity drain the solution from the tanks. Such a port would preferably be fitted with a removable screen filter 20 to retain small non-hydrolyzable materials that may have escaped from the basket during the digestion process. Alternatively, pumps may be used to drain the tanks of their contents.

However, any pump utilized in this apparatus should be made of stainless steel with all seals and liners made of a material capable of withstanding strong alkaline action; an example being TEFLON®. Materials such as glass, ceramics, rubber, and most synthetics should not be used due to their vulnerability to alkaline actions. The piping and valves used in the circulation of the solvent may be linked to or comprise the same piping and valves utilized in the draining and flushing of the tank. In addition, if a pump is utilized to circulate the highly basic solvent 12 this same pump may be utilized to drain the reaction mixture.

Preferred safety controls on any drainage system would include measurements of pH by port sampling or continuous flow analysis with input of both sets of data going to a manually or electronically controlled valving system. Specifically, manual or automated systems must receive information on the final pH of the solvent at the completion of the digestion process before dilution can be calculated and implemented in order to initiate discharge of the vessel.

An alternative embodiment of an apparatus for practicing the present invention is shown in FIG. 4, comprising a plurality of tanks, a highly basic solution 12 within the first tank 34, a less basic solution 37 in the second tank 36, a neutral solution 39 in the third tank 38, and means for removing the solutions 30 therein.

The first tank 34 may have additional modifications shown in FIG. 1, unlike the additional tanks, such as a heating means 18, a sealing means 14, an agitating means 24, and a pressurizing means 17. Since these modifications are only necessary for the tank in which the reaction actually takes place, any additional tanks would not require these modifications. Further comprising the alternative apparatus in FIG. 4 are a refrigeration means 40 for storage of the waste, a means for moving the permeable container 42, a ventilation means 26, a water supply means 28 and a disposal means 32.

As can be seen from FIG. 4, it is possible for the apparatus to utilize a plurality of tanks. The tanks may be located in proximity to one another such as in a linear or circular series. When a single tank is used, this tank will contain the highly basic solvent 12. However, when a plurality of tanks is used, the first tank 34 in the series may contain a highly basic solvent 12 and the second tank 36 and subsequent tanks containing a less basic solution. Preferably, the second tank 36 contains a solution 37 having a pH of approximately 10. The solution of the second tank 36 may be comprised of one percent sodium hypochlorite; i.e., a 1:5 dilution of household chlorine bleach and water. The third tank 38 in the series may contain a solution 39 having a pH of approximately 7, such as water. The second and third tanks may be utilized to rinse off the highly basic solvent 12 that remains upon the permeable container 22 and the solid non-hydrolyzable debris. This may be accomplished by moving the permeable container 22 and/or solid debris sequentially through the tanks. Use of all three tanks is optional as use of either 1, 2, 3 or more tanks is possible. When only two tanks are utilized, it is preferable for the second tank to contain a solution having a pH of approximately 7, such as water.

It may also be necessary to provide a means for moving the container 42 housing the waste therein. The means necessary to complete this function is highly dependent upon the amount of waste a intended to be disposed. If it is to be done in small amounts and, therefore small weights are involved, a less sophisticated or complex means could be used. Possible means range from simple winch and pulley systems to more mechanized apparatus such as forklifts, hydraulic apparatus, or mechanized winches. It may be advantageous that the moving means 42 be sized such that it can move the containers from tank 34 to tank 36 with a hood 26 remaining in place over the tanks.

A further component of the apparatus may include a freezer 40. As indicated above, it may be desirous to store the tissue or other matter containing infectious waste for a period of time before disposing of the animal tissue a freezer when disposal is not conducted on a daily basis.

Figure 5:
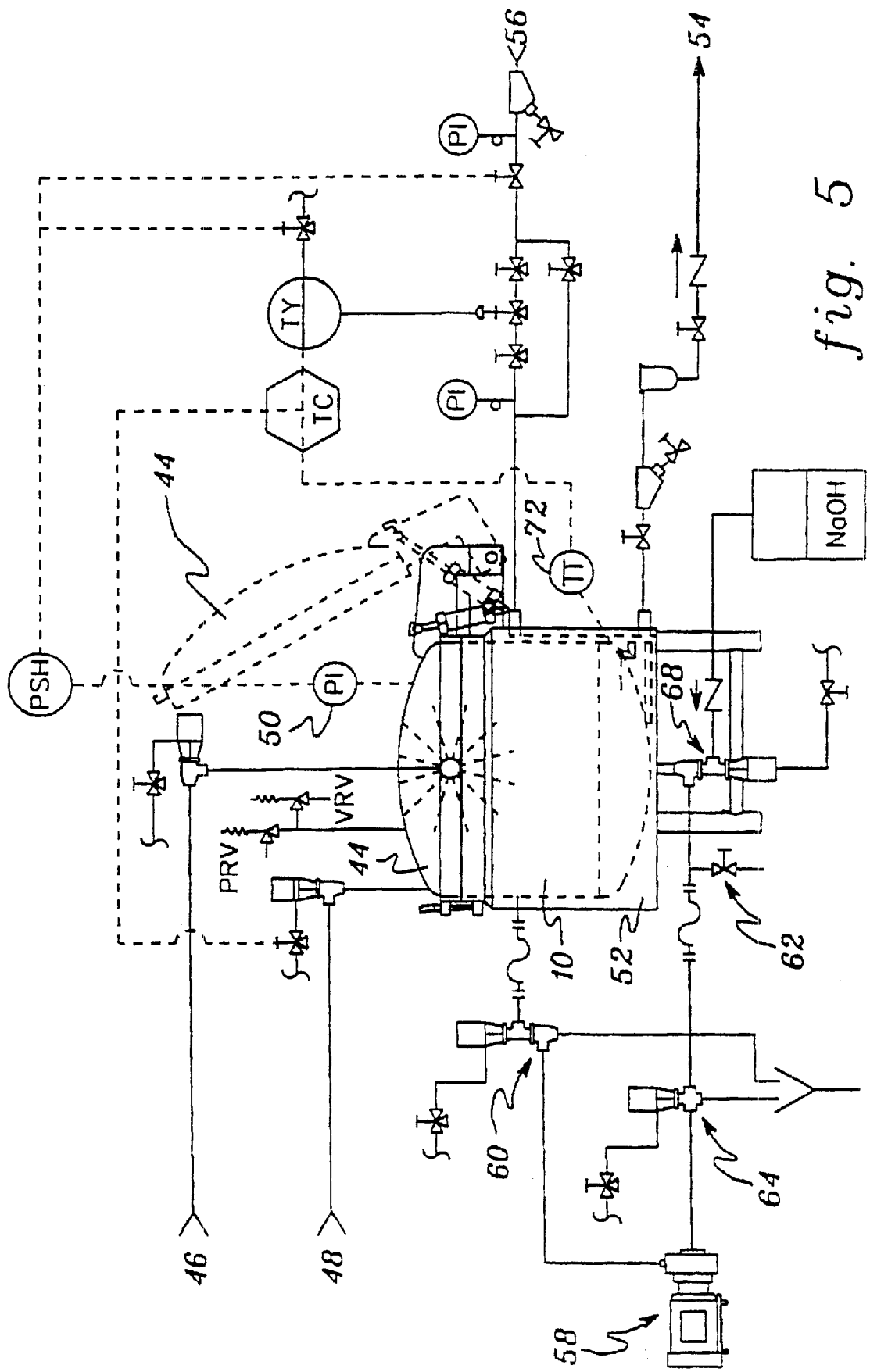
FIG. 5 shows a schematic drawing of an apparatus for practicing the present invention.

As can be seen in reference to FIG. 5, other embodiments capable of manual or automated operation may be designed without departing from the scope of the present invention. This particular embodiment discloses a sealable tank 10 having a top lid 44, a water inlet port 46, an air vent 48 and pressure gauge 50. A steam jacket 52 surrounds the length of the tank 10 and has separate condensate outlet 54 and steam inlet 56 on-off valves. Condensate outlet 54 may also be used as a cooling water inlet to circulate cooling water into jacket 52, and steam inlet 56 may be used to exit the cooling water from the jacket. A single pump 58 may be used and is connected to the various drainage and sampling ports via a system of connecting pipes and valves, such as the pump to vessel shut-off valve 60, the sampling valve 62, the pump to drainage shutoff valve 64 and the lower pipe drainage and alkali inlet valve 68. The bottom of tank 10 is also fitted with a temperature sensor 72. All of which may be run manually or by an automating means, such as a microprocessor connected to the various sensors, pumps and valves.

Although the invention has been described in the terms of the preferred embodiments, it is apparent to those skilled in the art that various modifications, substitutions, equivalents and other changes may be utilized without departing from the spirit of the invention.

We claim:

1. A method for treating regulated medical waste comprising the steps of:
   (a) providing a highly basic solvent;
   (b) immersing said regulated medical waste into said highly basic solvent, wherein said regulated medical waste contains infectious agents comprising hydrolyzable material, wherein said infectious agents are capable of causing infection in humans or animals and are selected from the group consisting of bacteria, organisms, and proteinaceous material; and
   (c) heating said highly basic solvent and said immersed regulated medical waste to a temperature greater than 130° C. and under a pressure greater than 2.79 atmospheres and for a time sufficient to digest said hydrolyzable material, whereby a sterile solution comprising non-toxic biodegradable materials and containing sterile solid waste free of said infectious agents is produced.

2. The method of claim 1, wherein said highly basic solvent has a pH of at least 12 up to about 14.

3. The method of claim 2, wherein step (c) is carried out at a maximum temperature of about 180° C.

4. The method of claim 2, wherein said temperature ranges from about 135° C. to about 180° C., and said pressure ranges from about 3.1 atmospheres to about 10 atmospheres, respectively.

5. The method of claim 4, wherein said temperature ranges from about 150° C. to about 155° C., and said pressure is about 5 atmospheres.

6. The method of claim 1, wherein said highly basic solvent comprises a mixture of water and an alkali metal hydroxide, alkaline-earth-metal hydroxide, or alkaline-earth metal oxide.

7. The method of claim 1, wherein said highly basic solvent also includes a detergent at a concentration of up to about 1% by weight.

8. The method of claim 1 further comprising in step (b) adding a hazardous waste solution into said highly basic solvent, wherein said hazardous waste solution also contains said infectious agents comprising hydrolyzable material.

9. The method of claim 8, wherein said hazardous waste solution comprises infectious agents in solution with a material selected from the group consisting of formaldehyde, glutaraldehyde, phenols, mixtures of formaldehyde and glutaraldehyde, mixtures of formaldehyde and phenols, and mixtures of glutaraldehyde and phenols.

10. The method of claim 1, wherein said regulated medical waste further contains lipid soluble hazardous material, said method further comprising between steps (b) and (c) the step of adding a paraffin or wax to said highly basic solvent containing said regulated medical waste, wherein upon heating in step (c) said lipid soluble hazardous material and said paraffin or wax are dispersed throughout said sterile solution.

11. The method of claim 10 further comprising after step (c) a cooling step, wherein upon cooling to room temperature, said lipid soluble hazardous material and said paraffin or wax separate from said sterile solution to form a solid lipid phase atop said sterile solution.

12. The method of claim 11 further comprising removing said solid lipid phase.

13. The method of claim 1, wherein said regulated medical waste further contains lipid soluble hazardous material, said method further comprising in step (c) adding a paraffin or wax to said highly basic solvent containing said regulated medical waste, wherein upon heating in step (c), said lipid soluble hazardous material and said paraffin or wax are dispersed throughout said sterile solution.

14. The method of claim 13 further comprising after step (c) a cooling step, wherein upon cooling to room temperature, said lipid soluble hazardous material and said paraffin or wax separate from sterile solution to form a solid lipid phase atop said sterile solution.

15. The method of claim 14 further comprising removing said solid lipid phase.

16. The method of claim 1 further comprising agitating, circulating, or stirring the highly basic solvent in step (c).

17. The method of claim 1 further comprising reducing the alkalinity of said sterile solution by dilution with water.

18. The method of claim 1 further comprising disposing of said sterile solution and said sterile solid waste.

19. The method of claim 1 further comprising the step of removing said sterile solid waste from said sterile solution.

20. A method for removing infectious agents from a hazardous waste solution comprising the steps of:
   (a) providing a highly basic solvent having a pH of at least 12 up to about 14;
   (b) contacting said hazardous waste solution containing said infectious agents and said highly basic solvent, wherein said infectious agents comprise hydrolyzable material, and wherein said infectious agents are capable of causing infection in humans or animals and are selected from the group consisting of bacteria, organisms, and proteinaceous material; and
   (c) heating said highly basic solvent and said hazardous waste solution to a temperature greater than 130° C. and at a pressure greater than 2.79 atmospheres and for a time sufficient to digest said hydrolyzable material, whereby a sterile solution comprising non-toxic biodegradable materials and containing sterile solid waste free of said infectious agents is produced.

21. The method of claim 20, wherein said hazardous waste solution comprises infectious agents in solution with a material selected from the group consisting of formaldehyde, glutaraldehyde, phenols, mixtures of formaldehyde and glutaraldehyde, mixtures of formaldehyde and phenols, and mixtures of glutaraldehyde and phenols.

22. A method for producing a sterile solution from a hazardous waste solution comprising the steps of:
(a) providing a highly basic solvent having a pH of at least 12 up to about 14;
(b) contacting said hazardous waste solution and said highly basic solvent, wherein said hazardous waste solution comprises hydrolyzable material selected from the group consisting of biological tissues, cells, or cell components, in solution with a material selected from the group consisting of formaldehyde, glutaraldehyde, phenols, mixtures of formaldehyde and glutaraldehyde, mixtures of formaldehyde and phenols, and mixtures of glutaraldehyde and phenols; and
(c) heating said highly basic solvent and said hazardous waste solution to a temperature greater than 130° C. and at a pressure greater than 2.79 atmospheres and for a time sufficient to digest said hydrolyzable material, whereby a sterile solution comprising non-toxic biodegradable materials and containing sterile solid waste is produced.

* * * * *